US00PP35111P2

(12) United States Plant Patent
Lee

(10) Patent No.: US PP35,111 P2
(45) Date of Patent: Apr. 18, 2023

(54) ***CLIFTONIA* PLANT NAMED 'BLCM05'**

(50) Latin Name: *Cliftonia monophylla*
Varietal Denomination: BLCM05

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 17/892,321

(22) Filed: Aug. 22, 2022

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226, 216, 263.1
CPC ..... A01H 5/00; A01H 5/02; A01H 6/00
See application file for complete search history.

*Primary Examiner* — June Hwu
(74) *Attorney, Agent, or Firm* — Cassandra Bright

(57) ABSTRACT

A new and distinctive *Cliftonia monophylla* plant, characterized by its fragrant pink flowers. Plants are upright in form, having a V-shape. Mature plants reach a height around 6 to 8 feet with a spread of around 4 to 5 feet. This controlled plant habit makes a useful ornamental landscape plant with very little maintenance. The new plant is a *Cliftonia*, typically useful for ornamental horticulture.

2 Drawing Sheets

Figure 1:
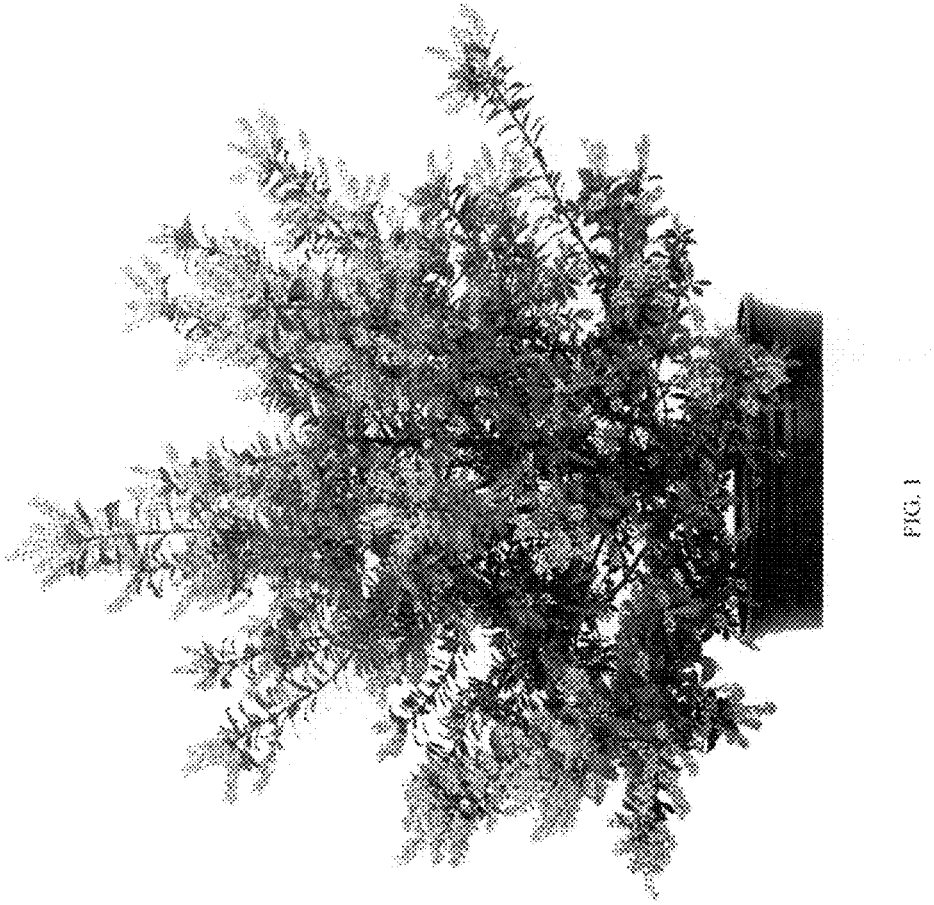

Latin name of the genus and species: *Cliftonia monophylla.*

Variety denomination: 'BLCM05'.

BACKGROUND OF THE INVENTION

The present invention relates to a new and distinct variety of *Cliftonia monophylla*, which has been named 'BLCM05'. *Cliftonia monophylla* is an evergreen flowering perennial shrub that is used as an ornamental plant in landscape and novelty horticulture.

The new variety resulted from an open-pollination breeding program including the unpatented pink-flowering varieties of *Cliftonia monophyla* 'Chipolo Pink' and 'Van Cleave'. The open-pollination occurred during 2009 at a commercial nursery in in Independence, La. Seeds resulting from this open-pollination were collected and sown during the Fall of 2009. The cultivar 'BLCM05' was selected in March of 2014 in a group of seedlings resulting from the open pollination.

The new variety 'BLCM05' was first asexually propagated by vegetative stem cuttings at a nursery in in Independence, La. during the Summer of 2014. Subsequent propagation has shown the features of the new variety are stable and reproduced true to type.

SUMMARY OF THE INVENTION

The cultivar 'BLCM05' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BLCM05'. These characteristics in combination distinguish 'BLCM05' as a new and distinct *Cliftonia* cultivar:

1. Pink flowers.
2. Easy to maintain in the landscape, maturing to a height of about 6 to 8 feet and a spread of about 4 to 5 feet with very little pruning.
3. Fragrant flowers, attractive to many pollinators.
4. Upright plant habit.
5. Hardy through zone 7.

PARENT COMPARISON

'BLCM05' is similar to the parent varieties in most horticultural characteristics, however, the new variety differs in the following:

1. The new variety matures to a height of about 6 to 8 feet. Both parent varieties mature to about 20 feet.

COMMERCIAL COMPARISON

'BLCM05' can be compared to the *Cliftonia* variety 'BLCM03', Plant patent application Ser. No. 17/892,317. Plants of the new cultivar 'BLCM05' are similar to plants of 'BLCM03' in most horticultural characteristics, however, plants of the new cultivar 'BLCM05' differ in the following:

1. Plants of 'BLCM05' achieve a larger mature height by almost double.
2. Plant habit of 'BLCM05' is upright, plant habit of 'BLCM03' is rounded.
3. Plants of 'BLCM05' are less dense than plants of 'BLCM03'.

'BLCM05' can be compared to the *Cliftonia* variety 'Chipolo Pink', unpatented. Plants of the new cultivar 'BLCM05' are similar to plants of 'Chipolo Pink' in in that both varieties produce pink flowers. However, plants of the new cultivar 'BLCM05' differ in the following:

1. This comparator is a small tree, growing to approximately 12 to 18 feet tall; the new variety is an upright shrub with a typical height around 6 to 8 feet.

BRIEF DESCRIPTION OF THE PHOTOGRAPHS

The accompanying photograph in FIG. 1 illustrates a typical plant of 'BLCM05' growing in a 3-gallon pot. The plant was grown outdoors in Loxley, Ala.

Figure 2:
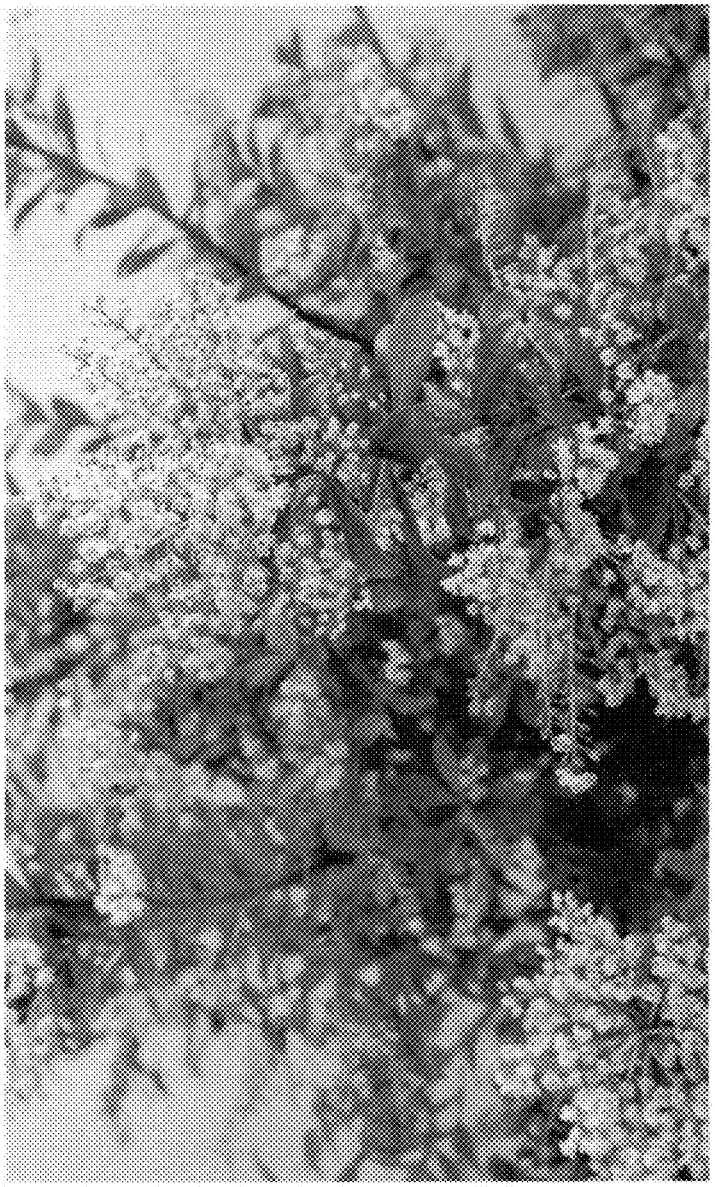

FIG. 2 illustrates in full color a close up of typical inflorescences of the new variety.

Plants photographed are approximately 2 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BLCM05' plants grown outdoors in Loxley, Ala. Plants are approximately 2 years old, in a 3 gallon nursery container. Measurements and numerical values represent averages of typical plant types.

Botanical classification: *Cliftonia monophylla* 'BLCM05'.

PROPAGATION

Propagation method: Typically by stem cuttings in Summer.

Root description: Fine, fibrous young roots, well branched. Colored near RHS Grey-Brown 199A.

PLANT

Growth habit: Upright, V-shaped shrub.

Height: Approximately 54 cm.

Plant spread: Approximately 58 cm.

Branching characteristics: 2 main basal branches, each splitting into 4 main lateral branches.

Primary branches:

Length of primary branches: Average 10 to 20 cm.

Diameter of primary branches: Average range 4 to 7 mm.

Primary branch strength: Very strong, difficult to break.

Primary branch color: Young primary branches near RHS Yellow-Green 144C, turning Greyed-Red 183C. Mature branches woody, colored near Greyed-Green 197A, heavily tinted Greyed-Purple N187A and N187B and slightly tinted Greyed-Red 182C.

Primary branch texture: Immature growth glabrous. Older growth scaly.

Lateral branches:

Length of lateral branches: Average range 5 to 10 cm.

Diameter of lateral branches: Average 3 mm.

Lateral branch strength: Strong.

Lateral branch color: Young primary branches upper surface near Greyed-Purple 187B, lower surface near Greyed-Purple 183B. Mature branches woody, colored near RHS Greyed-Purple 187A with scaliness colored near Grey-Green 197A on oldest growth.

Lateral branch texture: Immature growth glabrous. Older growth scaly.

Internode length: Average 2.5 cm to 6.0 cm.

Age of plant described: Approximately 2 years.

FOLIAGE

Leaf:

*Leaf.*—

*Type.*—Simple.

*Arrangement.*—Whorled towards branches ends, foliage on lower portion of branches sub-opposite.

*Average length.*—Approximately 3.2 cm to 3.6 cm.

*Average width.*—Approximately 9 to 14 mm.

*Shape of blade.*—Elliptic.

*Apex.*—acute.

*Base.*—Attenuate.

*Attachment.*—Sessile

*Margin.*—Entire.

*Texture of top surface.*—Glabrous.

*Texture of bottom surface.*—Glabrous.

*Color.*—Young foliage upper side: Near RHS Yellow-Green 144B, thin marginal coloration and center streaks near Greyed-Purple 185B. Young foliage under side: Near RHS Yellow-Green 144C, thin marginal coloration and center streaks near Greyed-Purple 185B. Mature foliage upper side: Near RHS Green 139A. Base Greyed-Purple 187B. Mature foliage under side: Near RHS Green 137C. Base Greyed-Purple 187B.

*Venation.*—Type: Pinnate. Venation color upper side: Near RHS Yellow-Green 144C. Venation color under side: Near RHS Green 138B.

FLOWER

Bloom period: Around April through May.

Inflorescence: Elongated, slightly weeping raceme.

Raceme:

*Length.*—Average 6 to 9 cm. Excluding peduncle.

*Diameter.*—Average 2.0 cm.

Raceme peduncle:

*Length.*—Average 1.5 cm.

*Diameter.*—2 to 3 mm.

*Color.*—Near RHS Yellow-Green N144D.

*Texture.*—Glabrous.

*Aspect.*—Slightly arched.

Raceme pedicel:

*Length.*—Average 5 mm

*Diameter.*—1 to 2 mm.

*Color.*—Youngest near Red-Purple N57C, mature near Red-Purple 58D, aging near Yellow-Green 153D.

*Texture.*—Glabrous.

*Aspect.*—Straight. Angle of attachment approximately 45° angle from peduncle.

*Peduncle rachis length.*—Average range 5 to 8 cm.

*Peduncle rachis color.*—Immature near Red-Purple N57C. Mature near 58D. Aging near Yellow-Green 153D.

Flowers:

*Quantity.*—Average 15 to 20 per raceme.

*Length.*—Average 5 mm

*Diameter.*—Average 5 to 6 mm.

*Facing direction.*—Outwardly facing.

*Fragrance.*—Significant sweet scent.

Petals:

*Petal number.*—6.

*Arrangement.*—Radial, slightly overlapping.

*Length.*—Approximately 3 to 4 mm.

*Aspect*.—Moderately upwardly cupped.
*Width*.—Approximately 3 mm.
*Apex*.—Acute.
*Base*.—Broad attenuate.
*Shape*.—Broad elliptic to obovate.
*Petal margin*.—Entire.
*Petal texture*.—Smooth, all surfaces.
*Color*.—Upper surface at first opening: Near RHS Greyed-Red 178C, large basal section near Red 49C. Under surface at first opening: Near RHS Greyed-Red 178C, large basal section near Red 49C. Upper surface at maturity: Near RHS Red-Purple 65D. Under surface at maturity: Near RHS Red 56A. Upper surface at fading: Near RHS Red-Purple 65D. Under surface at fading: Near RHS Red-Purple 65D.

Bud:
*Shape*.—Globular.
*Length*.—2 mm.
*Diameter*.—2 mm.
*Color*.—Near RHS Orange-Red N34C.

Calyx/sepals: Not present.

REPRODUCTIVE ORGANS

Stamens:
*Number*.—Approximately 9.
*Length*.—3 to 4 mm.
*Width*.—1 mm.
*Color*.—Near RHS Red 49D.

Anthers:
*Length*.—Approximately 1 mm.
*Color*.—Near RHS Greyed-Red 182A.
*Pollen*.—Scant, colored near RHS Red 37C.

Pistil:
*Number*.—1.
*Length*.—3 to 4 mm.
*Style*.—Highly reduced, less than 1 mm.
*Stigma*.—3 lobed, colored near Yellow-Green 144B, about 2 mm to 3 mm long.
*Ovary*.—Round approximately 1 mm in diameter. Colored near RHS Yellow-Green 144C.

OTHER CHARACTERISTICS

Disease and pest resistance: Not observed to be susceptible nor resistant to normal diseases and pests of *Cliftonia*.
Temperature tolerance: USDA Zones 7-10.
Drought tolerance: No tolerance for drought observed.
Fruit/seed production: Not observed to date.

What is claimed is:

1. A new and distinct cultivar of *Cliftonia monophylla* plant named 'BLCM05', substantially as described and illustrated herein.

* * * * *